(12) United States Patent
Mills et al.

(10) Patent No.: US 8,765,194 B2
(45) Date of Patent: Jul. 1, 2014

(54) NATURAL—TOPICAL ANALGESIC AND ANTI-INFLAMMATORY COMPOSITION

(76) Inventors: Michelle Mills, Antioch, TN (US); Michael Hutsell, Murfreesboro, TN (US)

( * ) Notice: Subject to any disclaimer, the term of this patent is extended or adjusted under 35 U.S.C. 154(b) by 56 days.

(21) Appl. No.: 13/565,676

(22) Filed: Aug. 2, 2012

(65) Prior Publication Data

US 2013/0040003 A1    Feb. 14, 2013

Related U.S. Application Data

(60) Provisional application No. 61/574,629, filed on Aug. 8, 2011.

(51) Int. Cl.
| | |
|---|---|
| *A61K 36/61* | (2006.01) |
| *A61K 36/53* | (2006.01) |
| *A61K 36/534* | (2006.01) |
| *A61K 36/76* | (2006.01) |
| *A61K 36/28* | (2006.01) |
| *A61K 8/35* | (2006.01) |
| *A61K 36/185* | (2006.01) |
| *A61K 8/92* | (2006.01) |
| *A61K 31/125* | (2006.01) |
| *A61K 8/97* | (2006.01) |
| *A61Q 19/00* | (2006.01) |
| *A61K 36/899* | (2006.01) |

(52) U.S. Cl.
CPC ............... *A61K 36/899* (2013.01); *A61K 36/76* (2013.01); *A61K 36/61* (2013.01); *A61K 36/28* (2013.01); *A61K 8/35* (2013.01); *A61K 36/185* (2013.01); *A61K 8/922* (2013.01); *A61K 31/125* (2013.01); *A61K 36/534* (2013.01); *A61K 8/97* (2013.01); *A61K 36/53* (2013.01); *A61Q 19/00* (2013.01)
USPC ........... 424/742; 424/747; 424/725; 424/775; 424/778

(58) Field of Classification Search
None
See application file for complete search history.

(56) References Cited

U.S. PATENT DOCUMENTS

| | | | |
|---|---|---|---|
| 2006/0105055 A1* | 5/2006 | Marenick et al. | 424/581 |
| 2009/0068128 A1* | 3/2009 | Waddington | 424/59 |
| 2009/0123570 A1* | 5/2009 | Warner et al. | 424/677 |
| 2014/0037767 A1* | 2/2014 | Hutsell et al. | 424/742 |

OTHER PUBLICATIONS

Website document entitled "Helichrysum Species". Jun. 2008. 3 pages. Downloaded from website http://www.aromahead.com/blog/2008/06/27/helichrysum-species/.*

* cited by examiner

*Primary Examiner* — Chris R Tate

(57) ABSTRACT

This invention replaces the practice of utilizing synthesized salicin compounds for use as anti-inflammatory components in topical pain relief compositions through the use of naturally occurring salicin in the form of *Salix alba* (white willow bark) botanicals. This invention is a compound of naturally occurring botanicals identified in the Natural Pharmacopeia as individually exhibiting anti-inflammatory and/or analgesic properties.

1 Claim, No Drawings

NATURAL—TOPICAL ANALGESIC AND ANTI-INFLAMMATORY COMPOSITION

CROSS-REFERENCE TO RELATED APPLICATIONS

This application claims priority to provisional U.S. Patent application No. 61/574,629 filed on Aug. 8, 2012.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

This invention is intended provide an alternative to synthetic topical pain relief preparations. This invention contains natural, botanical extracts and essential oils in lieu of synthetic analgesics and fragrance, replacing synthetic salicin based anti-inflammatory preparations.

BRIEF SUMMARY OF THE INVENTION

The invention is an emulsion of natural trans-dermal carriers and analgesic and anti-inflammatory components including *Salix alba* (White Willow Bark) extract. The cream is compounded by combining the jojoba oil base with *Salix alba* (White Willow Bark), the natural botanical extracts *Helicrysum Gymnocephalum, Lavendula Officinalis* (Lavender), *Pelargoneum Graveolens* (Egyptian Geranium), *Mentha viridis* (Spearmint), *Eucalyptus* Globulus (Eucalyptus), *Rosmarinus Officinalis* (Rosemary), crystalline menthol and crystalline camphor. The invention is intended as a topical pain relief agent for external use only. It is designed to relieve muscle and joint pain when massaged into the affected area of the body and to prevent subsequent pain through the cumulative effect of the natural analgesics contained therein.

BRIEF DESCRIPTION OF THE SEVERAL VIEWS OF THE DRAWING(S)

Not Applicable

DETAILED DESCRIPTION OF THE INVENTION

This invention replaces the practice of utilizing synthesized salicin compounds for use as anti-inflammatory components in topical pain relief compositions through the use of naturally occurring salicin in the form of *salix alba* (white willow bark) botanicals. This invention is a compound of naturally occurring botanicals identified in the Natural Pharmacopeia as individually exhibiting anti-inflammatory and/or analgesic properties. The compound is unique in that the addition of *Helicrysum Gymnocephalum* appears to enhance the absorption of the salicin contained in *Salix Alba* thus providing a superior product formerly unattainable using naturally occurring salicins. This combination of *Helicrysum Gymnocephalum* essential oil and *Salix alba* extract when combined with *Eucalyptus Globules* essential oil, *Lavandula Angustifolia* essential oil, *Pelargonium Graveoleus* essential oil, *Mentha Viridis* essential oil, Camphor, and *Mentha Avrensis* together constitute this unique invention.

The resulting compound is then incorporated into a bulk carrier material for proper dilution and stability, and for use as a convenient delivery mechanism. The resulting compound is a shelf stable off-white viscous cream with a menthol/botanical like odor. The invention is utilized by applying small amounts directly to areas of the human body affected by various types of pain.

TABLE 1

A complete description of included components follows:

| INCI Names | CAS Nos: | Concentration: |
|---|---|---|
| Water | 7732 18 5 | >30% to 100% |
| Mineral Oil | 8012 95 1 | >3% to 10% |
| Cetyl Alcohol | 36653 82 4 | >3% to 10% |
| Stearic Acid | 57 11 4 | >3% to 10% |
| *Mentha Avrensis* (menthol) | 216-51-5 | >3% to 10% |
| Stearyl Alcohol | 112 92 5 | >1% to 3% |
| Cetearyl Alcohol | 67762 27 0 | >1% to 3% |
| Cetereth 20 | 68339 49 6 | >1% to 3% |
| Propylene Glycol | 57 55 6 | >1% to 3% |
| Camphor | 76 22 2 | >1% to 3% |
| Isopropyl Palmitate | 142 91 6 | >0.1% to 0.3% |
| *Prunus Amygoalus* Dulcis Oil | 8007 69 0 | >0.1 to 0.3% |
| Glycol Monostearate S/E | 111 60 4 | >0.3% to 1% |
| Phenoxy Ethanol | 122 99 6 | >0.3% to 1% |
| Caprylyl Glycol | 11117 86 6 | >0.3% to 1% |
| *Simmondsia Chinensis* (Jojoba) Seed Oil | 61789 91 1 | 0.1% or less |
| *Salix Alba* (white willow) bark extract | N/A | >1% to 3% |
| *Eucalyptus Globules* Oil | 8000 48 4 | >1% to 3% |
| *Lavandula Angustifolia* (Lavender) Oil | 8000 28 0 | >0.3% to 1% |
| *Pelargonium Graveoleus* (Geranium) Oil | 8000 46 2 | >0.3% to 1% |
| *Helicrysum Gymnocephalum* Flower Oil | N/A | >0.3% to 1% |
| *Mentha viridis* (Spearmint) Oil | 8008 79 5 | >0.3% to 1% |
| Citric Acid | 77 92 9 | >0.3% to 1% |

The invention claimed is:

1. A cosmetic composition for the management of pain comprising:
    *Salix alba* (white willow) bark extract, in an amount by weight of about 1% to 3%;
    *Helichrysum gymnocephalum* flower essential oil in an amount by weight of about 0.03% to 1%;
    effective amounts of *Mentha avrensis* (menthol), camphor, *Eucalyptus* globules, *Lavandula angustifolia* (lavender) oil, *Pelargonium graveoleus* (geranium) oil, and *Mentha viridis* (spearmint) oil; and
    a cosmetic cream substrate.

* * * * *